(12) United States Patent
Steinbaugh et al.

(10) Patent No.: US 10,321,917 B2
(45) Date of Patent: Jun. 18, 2019

(54) TOURNIQUET BELT

(71) Applicant: RevMedx, Inc., Wilsonville, OR (US)

(72) Inventors: John Steinbaugh, Wilsonville, OR (US); Andrew Barofsky, Lake Oswego, OR (US)

(73) Assignee: RevMedx, Inc., Wilsonville, OR (US)

( * ) Notice: Subject to any disclaimer, the term of this patent is extended or adjusted under 35 U.S.C. 154(b) by 295 days.

(21) Appl. No.: 14/740,084

(22) Filed: Jun. 15, 2015

(65) Prior Publication Data
US 2015/0359542 A1 Dec. 17, 2015

Related U.S. Application Data

(60) Provisional application No. 62/011,733, filed on Jun. 13, 2014, provisional application No. 62/048,333, filed on Sep. 10, 2014.

(51) Int. Cl.
*A61B 17/132* (2006.01)

(52) U.S. Cl.
CPC ................................ *A61B 17/1327* (2013.01)

(58) Field of Classification Search
CPC .................................................. A61B 17/1327
See application file for complete search history.

(56) References Cited

U.S. PATENT DOCUMENTS

| | | | | |
|---|---|---|---|---|
| 34,112 A * | 1/1862 | Lambert | ............ | A61B 17/1327 24/186 |
| 1,870,052 A * | 8/1932 | Jones | ................ | A61B 17/1327 606/203 |
| 3,587,584 A * | 6/1971 | Keller | ................. | A61B 17/135 606/202 |
| 5,540,714 A * | 7/1996 | Payne, Jr. | .......... | A61B 17/1322 606/201 |
| 7,947,061 B1 * | 5/2011 | Reis | .................... | A61B 17/1322 606/203 |
| 8,652,164 B1 * | 2/2014 | Aston | ................ | A61B 17/1327 606/203 |
| 2005/0049630 A1 * | 3/2005 | Ambach | ............ | A61B 17/1327 606/203 |
| 2005/0113866 A1 * | 5/2005 | Heinz | ................ | A61B 17/1327 606/203 |
| 2005/0267518 A1 * | 12/2005 | Wright | ................. | A61B 17/132 606/203 |
| 2005/0273134 A1 * | 12/2005 | Esposito | ............ | A61B 17/1327 606/203 |
| 2007/0005107 A1 * | 1/2007 | Janota | ................ | A61B 17/1322 606/203 |
| 2009/0062842 A1 * | 3/2009 | Esposito | ............ | A61B 17/1327 606/203 |
| 2010/0049241 A1 * | 2/2010 | Persson | .............. | A61B 17/1327 606/203 |
| 2010/0057120 A1 * | 3/2010 | Kirkham | ............ | A61B 17/1322 606/203 |

(Continued)

*Primary Examiner* — Phong Son H Dang

(74) *Attorney, Agent, or Firm* — Schwabe, Williamson & Wyatt, P.C.

(57) ABSTRACT

Embodiments provide a tourniquet that may be used as a daily wear belt. A tourniquet belt may include an elongate belt having a first end and a second free end; a securing element coupled to the elongate belt at the first end of the elongate belt; and a separate tightening element coupled to the elongate belt, wherein the tightening element is selectively actuable to tighten or loosen the tourniquet belt.

9 Claims, 27 Drawing Sheets

(56) References Cited

U.S. PATENT DOCUMENTS

| | | | | |
|---|---|---|---|---|
| 2011/0271494 | A1* | 11/2011 | Bellamy | A44B 11/18 24/16 R |
| 2012/0041351 | A1* | 2/2012 | Nolan | A61F 13/085 602/13 |
| 2012/0071917 | A1* | 3/2012 | McDonald | A61B 17/1322 606/203 |
| 2012/0215254 | A1* | 8/2012 | Brub | A61B 17/1327 606/203 |
| 2013/0110019 | A1* | 5/2013 | Hopman | A61B 17/135 602/13 |
| 2014/0277103 | A1* | 9/2014 | Esposito | A44B 11/258 606/203 |
| 2014/0350408 | A1* | 11/2014 | Goldman | A61B 5/4887 600/473 |
| 2015/0216536 | A1* | 8/2015 | Hopman | A61B 17/1322 606/202 |
| 2016/0089152 | A1* | 3/2016 | Henderson | A61B 17/1325 606/203 |
| 2016/0367262 | A1* | 12/2016 | Burke | A61B 17/1322 |

* cited by examiner

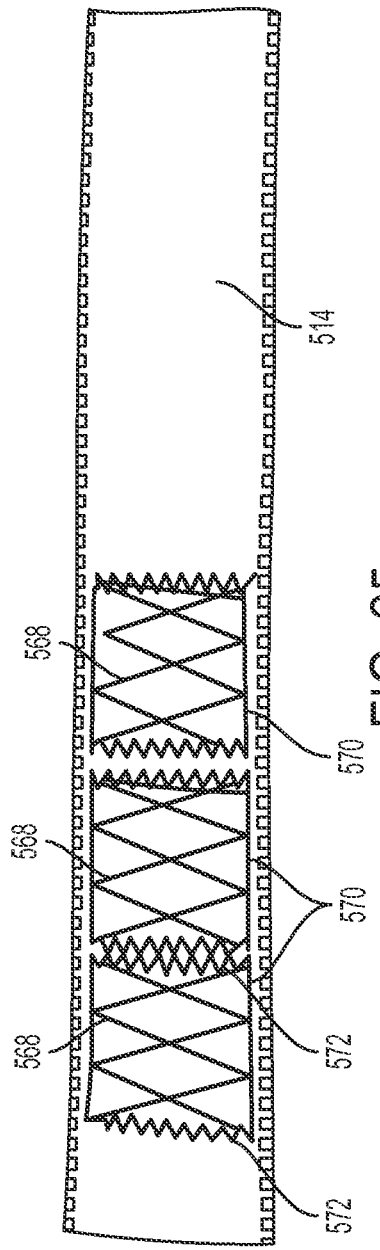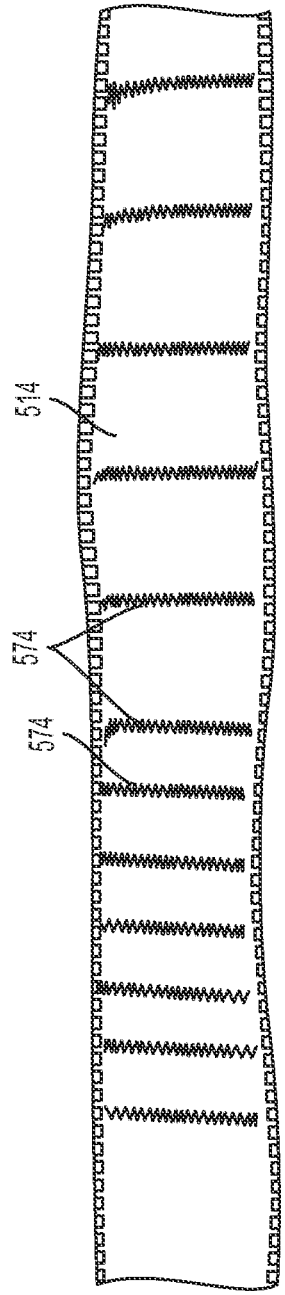

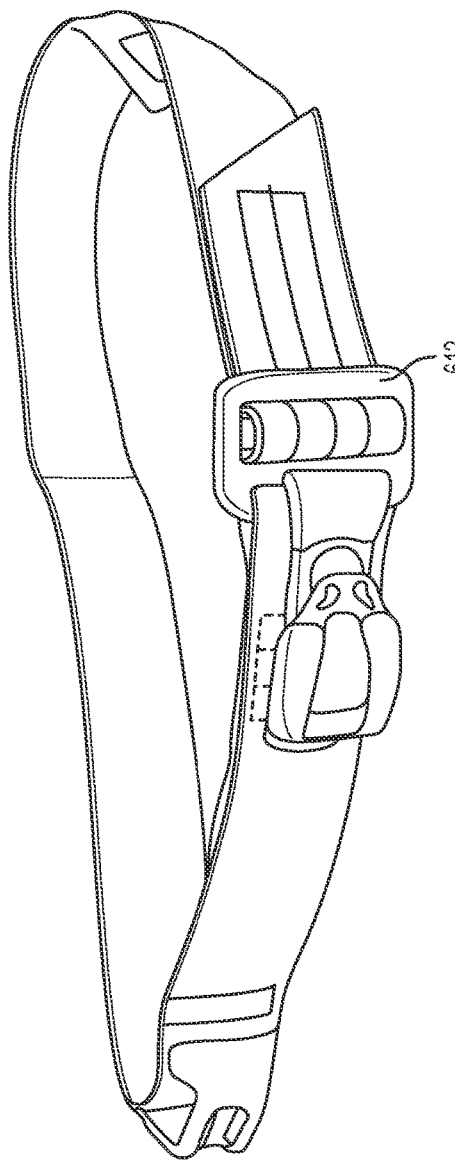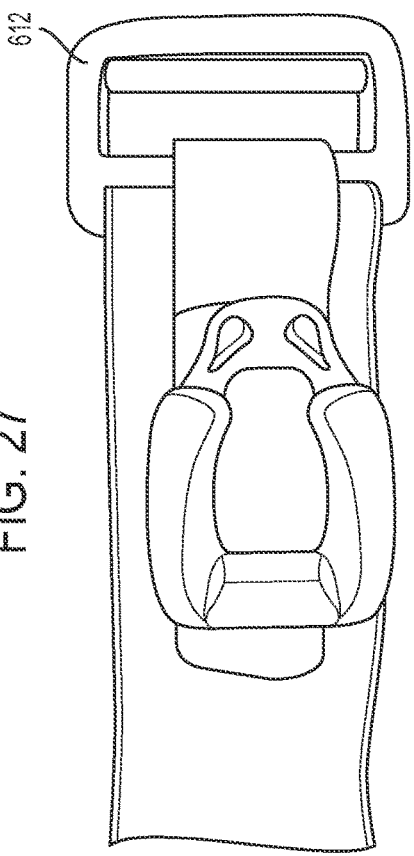

TOURNIQUET BELT

CROSS-REFERENCE TO RELATED APPLICATIONS

The present application claims priority to U.S. Provisional Patent Application No. 62/011,733, filed Jun. 13, 2014, entitled "Tourniquet Apparatus" and to U.S. Provisional Patent Application No. 62/048,333, filed Sep. 10, 2014, entitled "Tourniquet Apparatus" the entire disclosures of which are hereby incorporated by reference in their entirety.

TECHNICAL FIELD

Embodiments herein relate to functional apparel, and, more specifically, to a tourniquet that can be worn as a belt.

BACKGROUND

Tourniquets are used in a variety of medical contexts, including military, emergency medical services, and civilian scenarios. A properly constructed tourniquet is critical to function and efficacy.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 25 and 26 illustrate various stitching patterns in accordance with various embodiments;

FIGS. 27-30 illustrate various friction buckles in accordance with various embodiments.

DETAILED DESCRIPTION OF DISCLOSED EMBODIMENTS

Figure 1:
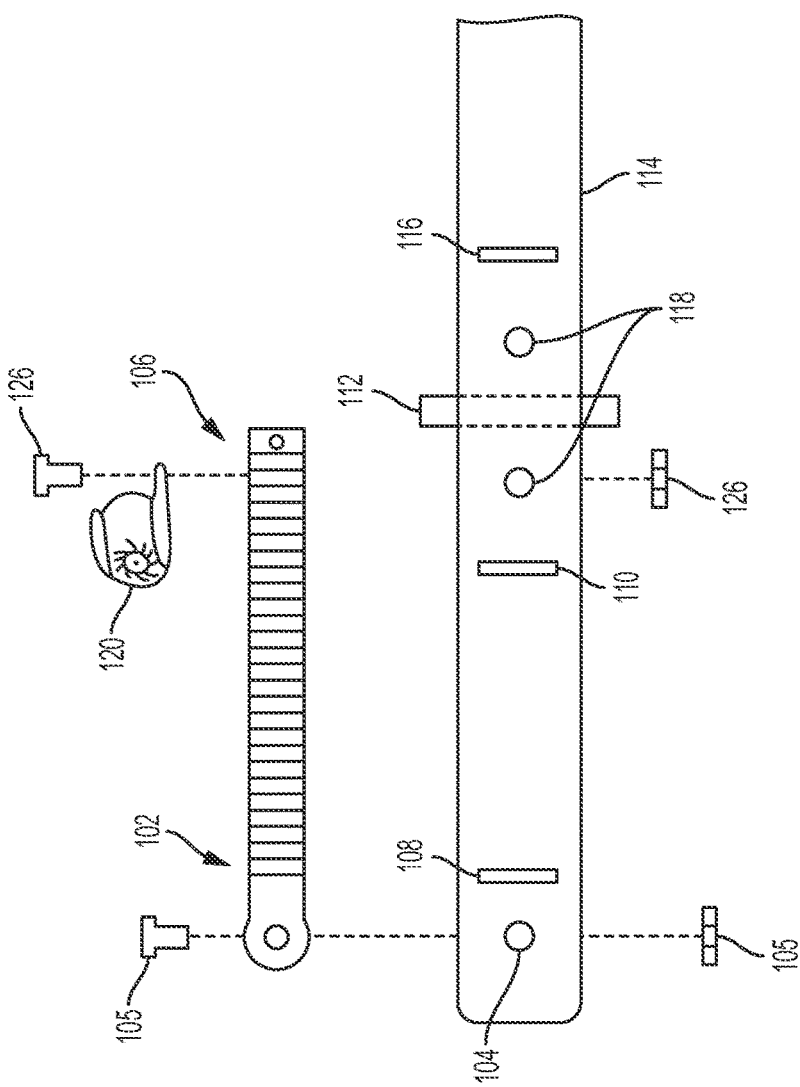
FIGS. 1 and 2 illustrate various elements used in the construction of a tourniquet belt in accordance with various embodiments.
Figure 2:
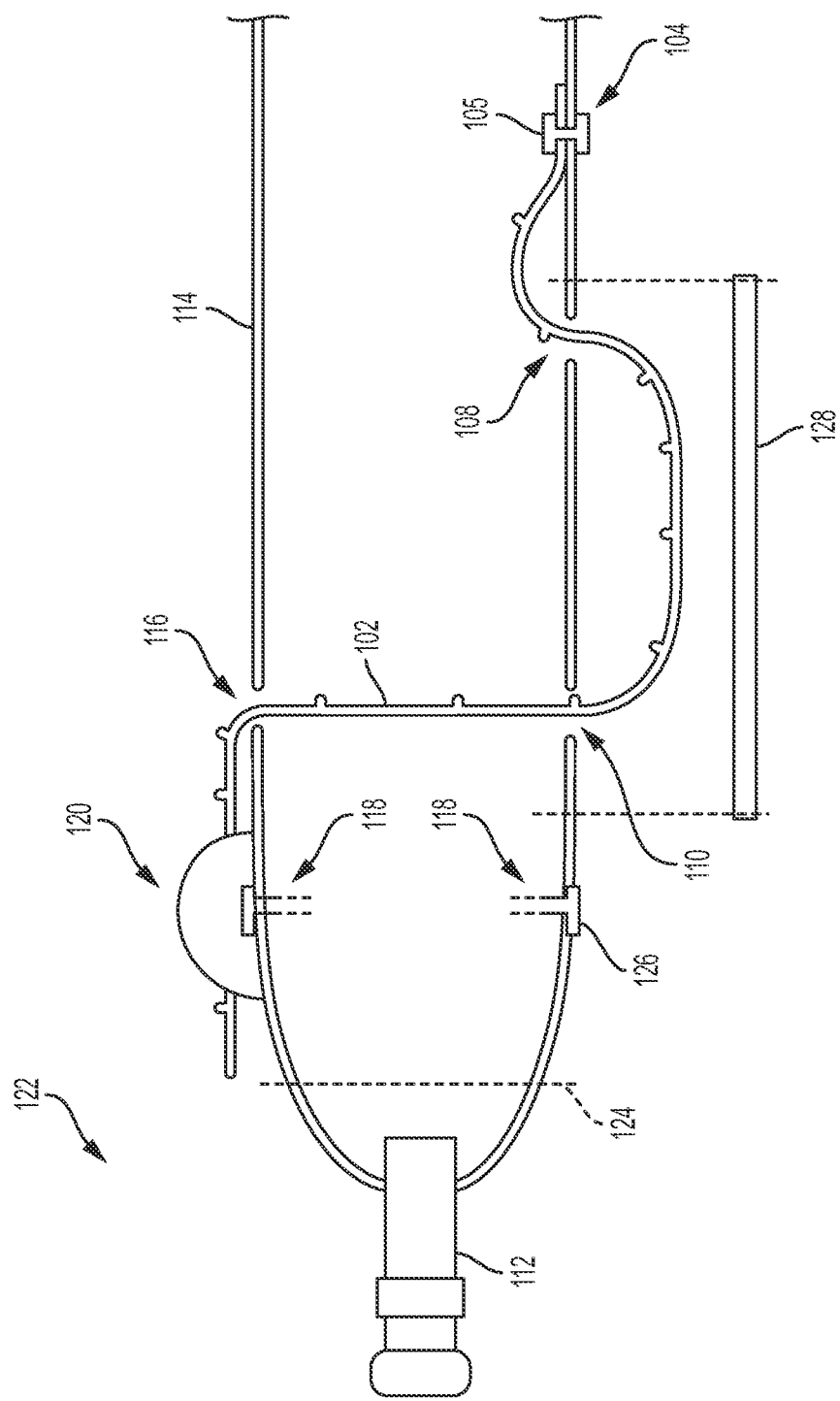
Figure 3:
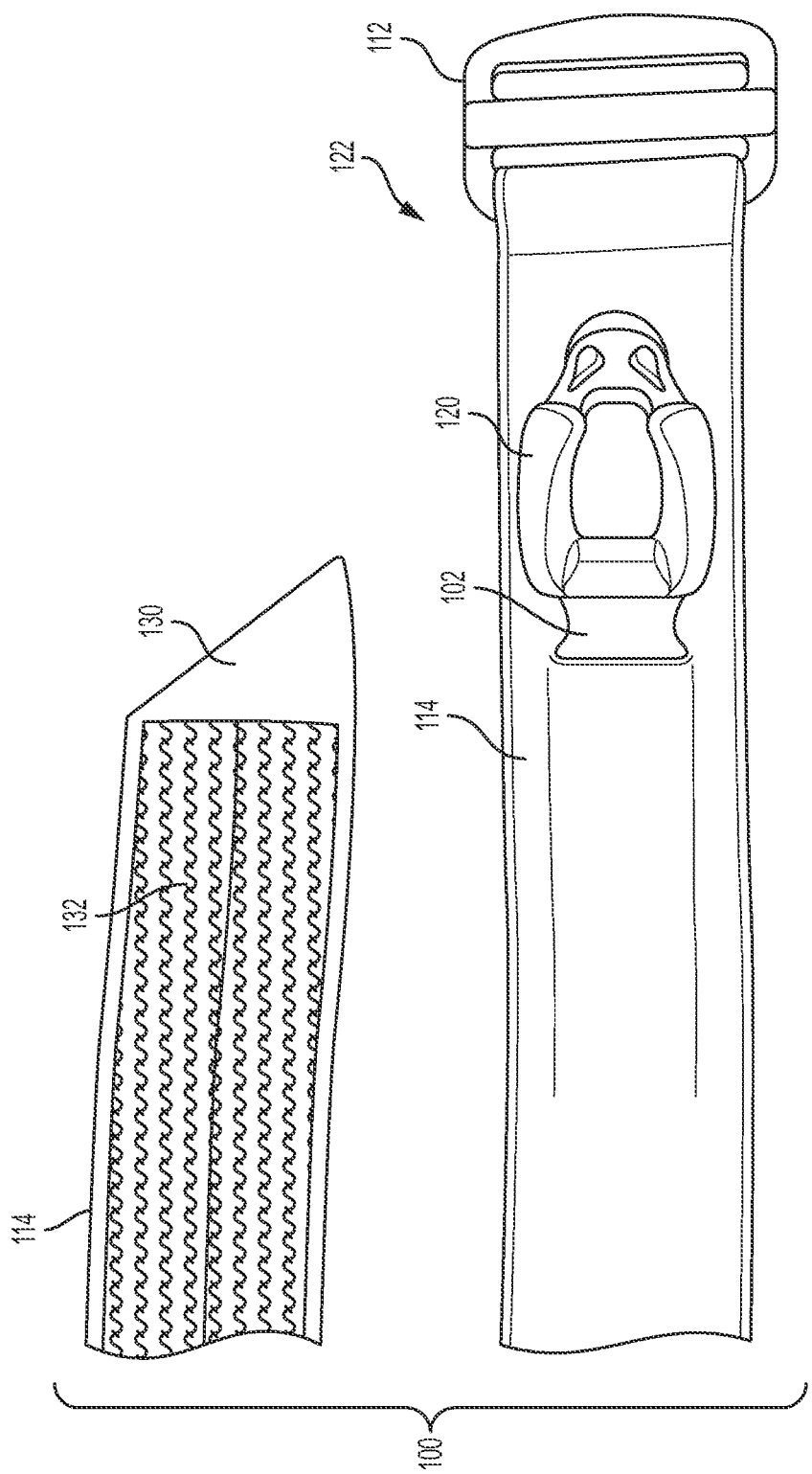
FIGS. 3-7 illustrate a tourniquet belt in accordance with various embodiments.
Figure 4:
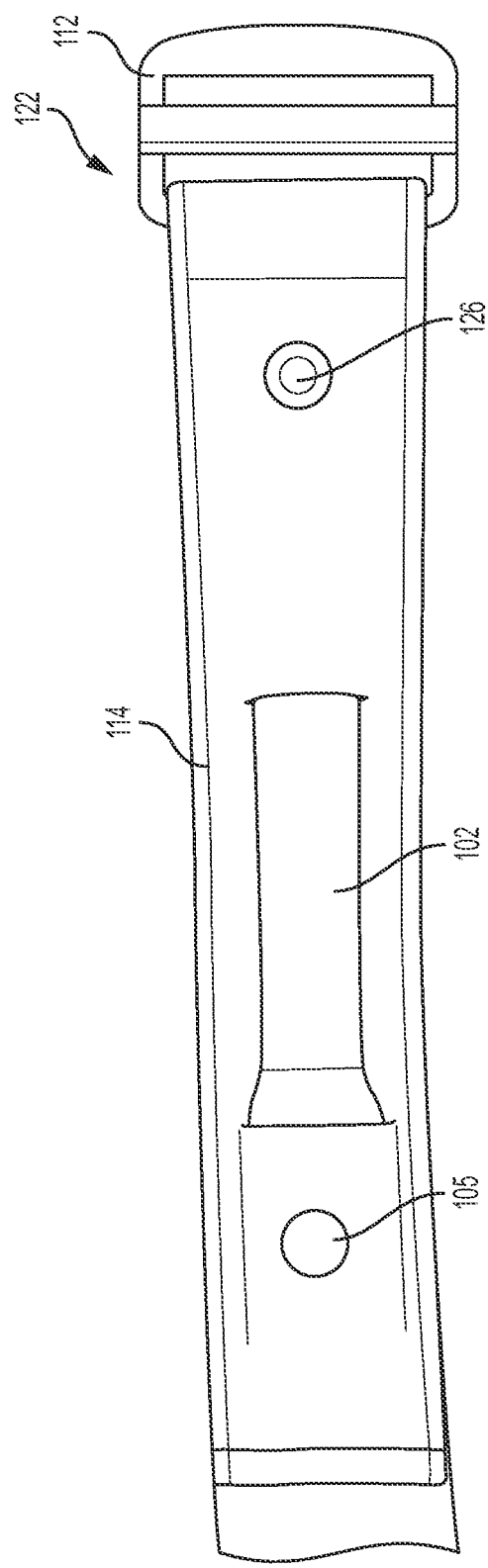
Figure 5:
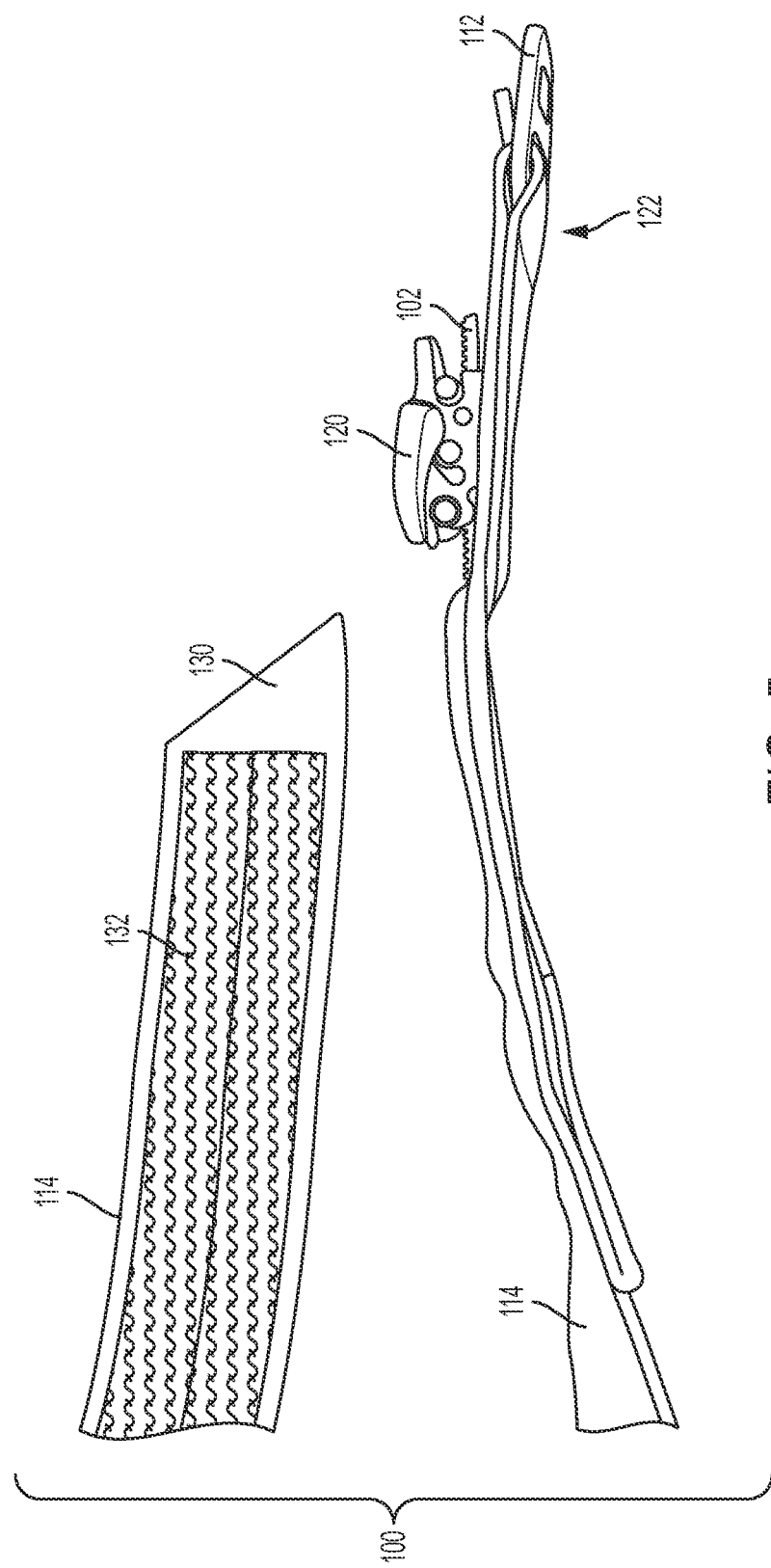
Figure 6:
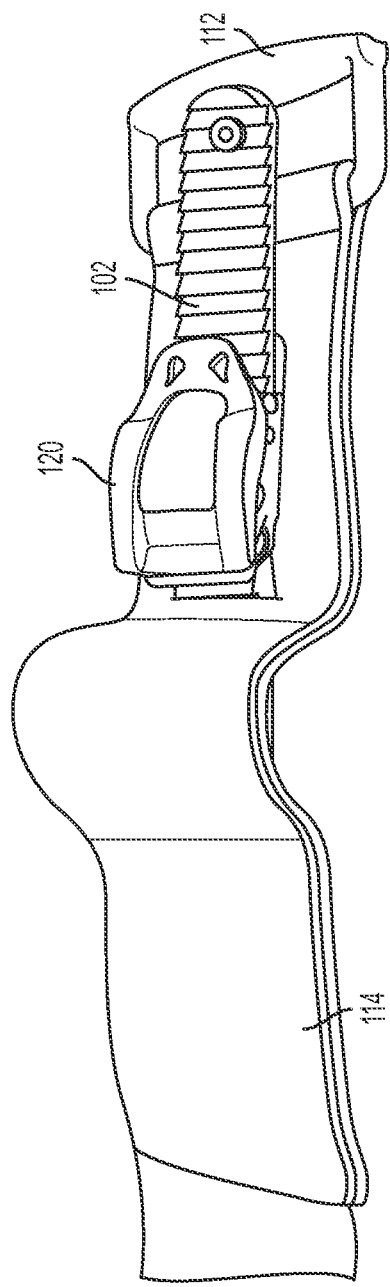
Figure 7:
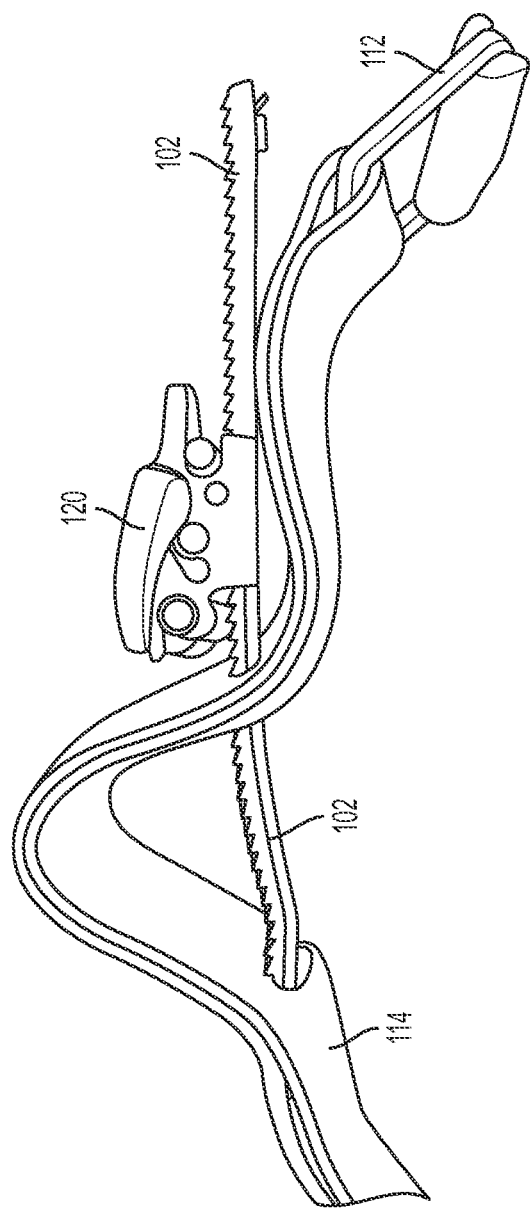

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments herein provide a tourniquet that may be used as a daily wear belt.

A tourniquet belt may include an elongate belt having a first end and a second free end; a securing element coupled to the elongate belt at the first end of the elongate belt; and a separate tightening element coupled to the elongate belt, wherein the tightening element is selectively actuable to tighten or loosen the tourniquet belt.

A first set of embodiments includes a first securing element and a secondary tightening element that allows the belt to be used as a tourniquet. FIGS. 1-10 provide various representations of such an embodiment.

The belt may include a band formed from any suitable, standard belt material that is also durable enough to withstand the tension of tourniquet tightening. Examples of suitable materials include flexible webbing, leather, and other sufficiently durable and flexible materials that may be used as discussed herein.

The belt may be an elongate belt having a width and length consistent with existing belts. For example, the belt may be between approximately 1 inch and approximately 3 inches in width. The belt may be provided in different lengths to accommodate different waist sizes (e.g., XS, S, M, LG, XL, XXL). Some implementations of the belt may be provided in widths and lengths consistent with men's sizes and other implementations of the belt may be provided in widths and lengths consistent with women's sizes.

The belt may have a securing end, having a securing element, such as a buckle, and a free end. In an embodiment, during use as a belt, the free end may feed through the securing element (such as a buckle) to secure the belt around the wearer's waist.

In an embodiment, a buckle, such as a friction buckle, may be secured to the belt via a seam or other attachment mechanism, and may take any desired form. In some embodiments, it may be particularly advantageous for the friction buckle to be a friction bar buckle, a double D-ring, a cleat, or another friction-based buckle or ring mechanism. In embodiments, such securing elements also have the ability to be selectively adjusted using the standard friction bar adjustment when the belt is in use as a tourniquet. In some embodiments, a friction buckle may include a female snap buckle secured to the first end and a male snap buckle secured to the free end (or vice versa), with a friction mechanism securing the belt to the male snap buckle.

In some embodiments, during use as a belt, the free end may not necessarily feed through the securing element in the arrangement necessary to take advantage of friction-securing properties, but may instead be simply looped through the securing element and be fastened to itself. For example, one face of the free end of the belt may have a hook or loop material secured to it, and the same face of the belt (but further away from the free end) may have a complementary material so that, when the free end is looped through the securing element (such as a buckle), the free end may be secured to the belt via the hook/loop mechanism. In some embodiments, other fastening elements may be used instead of or in addition to hook/loop, such as snaps or buttons.

In some embodiments, the free end may include a loop of material to assist in tightening the belt when used as a tourniquet using a thumb or the teeth, thus reducing circumferential slipping during the tightening process.

In some embodiments, the belt may include a ladder strap permanently attached to the belt at a position closer to the first securing end than to the free end. A ladder strap may be a plastic strap with raised portions that can be used with a ratcheting buckle such that, as the ratcheting buckle is ratcheted (e.g., via a ratcheting arm, as known), the ladder strap is fed through and secured in the ratcheting buckle. As discussed below, the belt may have a ratcheting buckle that may be used in conjunction with the ladder strap to adjust the belt when used as a tourniquet.

The belt may include holes and slots for the mounting of the ladder strap and the ratcheting buckle. As shown in FIG. 1, the ladder strap 102 may be fixed to hole 104 using a rivet or grommet 105. In some embodiments, other attachment mechanisms may be used to fix the ladder strap to the belt, such as sewing or heat fusing. The end 106 of ladder strap 102 may be routed down through the slot 108 and back up through the slot 110, as shown in the exaggerated exploded view of FIG. 2. The friction buckle 112 may then be slid on the belt 114 and the belt 114 may be folded over and around the friction buckle 112 so that the slots 110 and 116 are aligned and the two holes 118 are aligned.

The end 106 of the ladder strap 102 may then be routed through the slot 116 and inserted into the ratcheting buckle 120. The friction buckle 112 may then be secured at the friction buckle end 122 by a seam 124 (e.g., a sewn or fused seam). The ratcheting buckle 120 is then attached to the belt 114 using a rivet 126 through the holes 118. In some embodiments, the ratcheting buckle 120 may be secured to the belt using a non-rivet mechanism, such as glue/adhesive.

Figure 17:
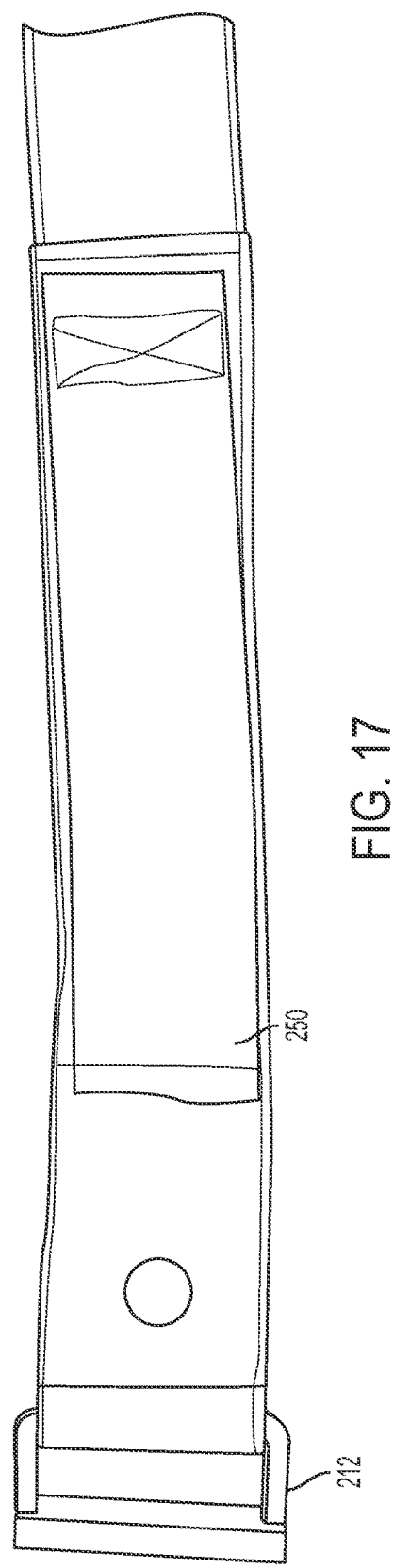

Overlapping layers of belt material may be sewn or otherwise joined together (e.g., at the long edges). A panel 128, illustrated in FIGS. 2 and 17, may be secured to the belt 114 so as to cover the ladder strap 102 and the slots 108 and 110. In some embodiments, the panel 128 may be formed from an elastic material that may be stretched before it is secured (e.g., by sewing or fusing) to the belt 114 (e.g., at the ends of the panel proximate to the slots 108 and 110). The elastic force of the panel 128 may not be strong enough to distort the belt when in regular use, but the memory of the elastic material may be sufficient for the panel 128 to "shrink" when the ratcheting buckle/ladder strap mechanism is used to tighten the belt during use as a tourniquet, as discussed below. As noted above, the free end 130 (FIG. 3) of the belt 114 may use a hook and loop material 132 or other mechanism to hold down the free end 130. During use as a belt, the ladder strap 102 may lay flush against the belt 114 either on one surface of the belt 114 (such as coupled on one side of the belt), or passing through the belt 114 and contacting two surfaces of the belt 114, as shown for example in FIGS. 3-7.

Figure 8:
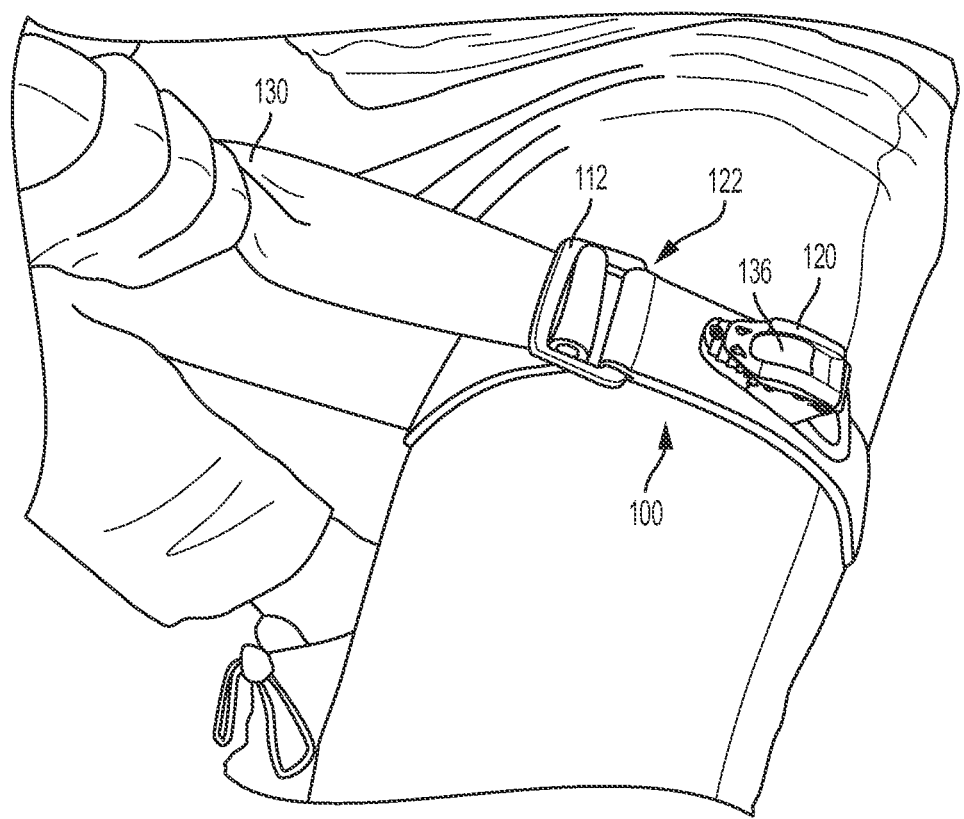
FIGS. 8-10 illustrate a tourniquet belt in use as a tourniquet in accordance with various embodiments.

Upon receiving a severe injury requiring the use of a tourniquet, the wearer may take off her belt and initially attach it around the injured limb tightly using the securing element, such as the friction buckle 120 shown in FIG. 8. Tightening may be achieved by pulling on the free end 130 in the appropriate direction, as shown.

Figure 9:
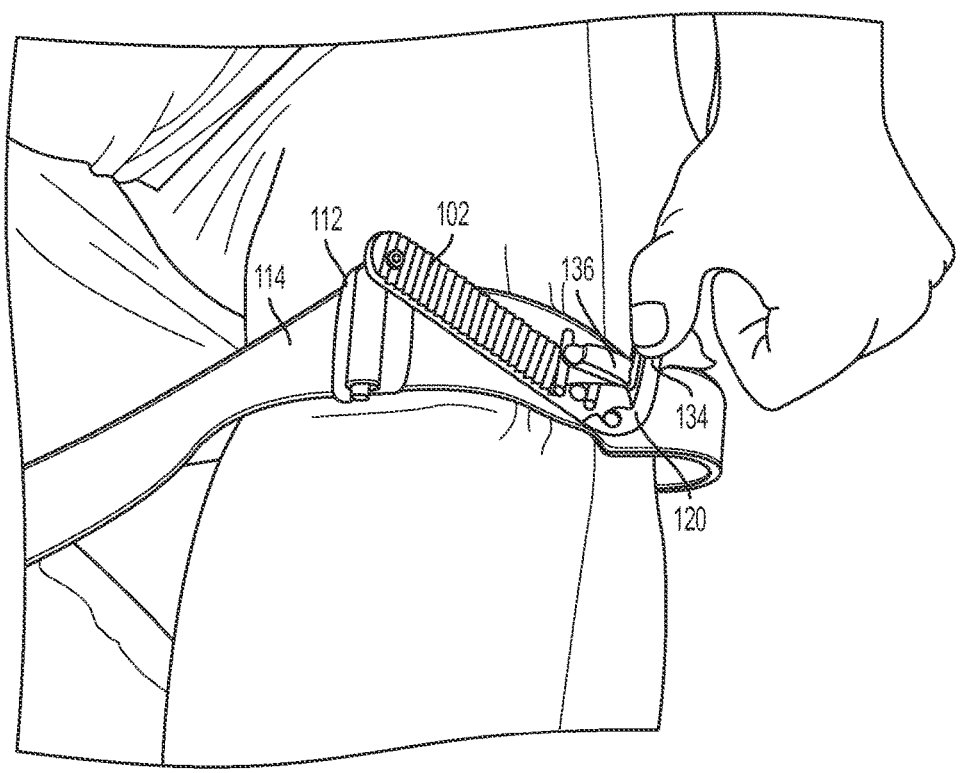
Figure 10:
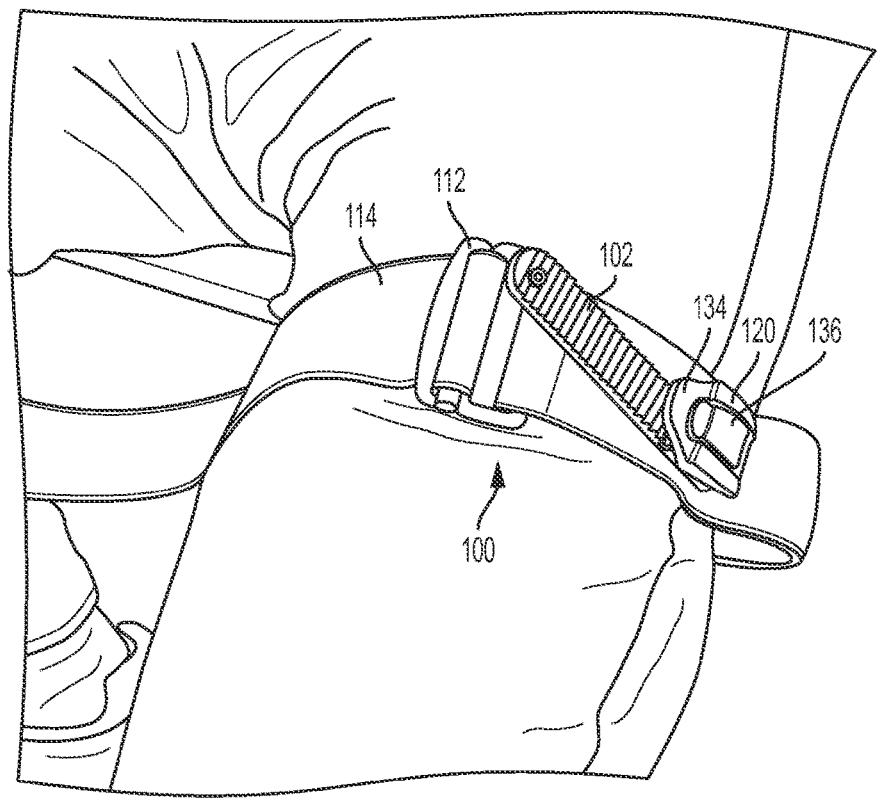

Once the friction buckle 112 has been used to attach the belt 114 tightly above the injury, the wearer may then operate the ratcheting buckle 120 by cranking/lifting the handle 134, as shown in FIG. 9. This may advance the ladder strap 102 through the ratcheting buckle 120, further tightening the belt 114 until the artery in the injured limb is compressed and the bleeding has stopped or adequately slowed, as shown in FIG. 10.

To release ratcheting buckle 120 and release tension on belt 114, the wearer may activate a release 136. The release 136 may be activated by lifting a lever/handle or depressing a button.

FIGS. 6, 7, 9, and 10 illustrate that, as the ratcheting buckle 120 is ratcheted, the belt 114 may gather away from the ladder strap 102 and away from the limb around which the belt 114 is tightened. This represents an improvement relative to conventional tourniquets, many of which are designed such that support material gathers between the tourniquet and the user's limb as the tourniquet is tightened. This "bunching" creates pressure points on the limb, causing discomfort to the wearer and cutting off the blood supply at inappropriate locations, thereby potentially damaging tissue.

In some embodiments, the panel 128 discussed above with reference to FIG. 2 may act as a barrier between the ladder strap 102 and the wearer's body to prevent the wearer's skin from getting pinched between the ladder strap 102 and the slots 110 and 116, or abraded during ratcheting. When the panel 128 is a "pre-stretched" elastic material, the tightening of the belt 114 via the ratcheting buckle/ladder strap mechanism may allow the panel to relax, thereby remaining taut and not bunching between the belt and the wearer's skin.

As shown in FIGS. 1-10, in some embodiments, the ratcheting buckle 120 is on the outside of the belt 114 when the tourniquet belt 100 is in normal use, and not trapped between the belt 114 and the wearer (an arrangement likely to cause discomfort). Additionally, the ratcheting buckle 120 is located close to the friction buckle 112, and thereby close to the center of the front of the wearer's body. In particular, the ratcheting buckle 120 may be located closer to the center of the front of the wearer's body than to the wearer's side. This position for the ratcheting buckle 120 may be advantageous in that the ratcheting buckle 120 is unlikely to interfere with equipment traditionally worn on a wearer's belt, particularly when the wearer is a law enforcement officer, soldier, emergency responder, or other professional. For such wearers, belts are used to carry holsters, pagers, pepper spray, tools, medical supplies, and other job-essential items. Because a belt buckle is traditionally located in the center front of a wearer's body, that area is traditionally free from these other items, while much of the rest of the belt may be occupied. Thus, positioning the ratcheting buckle 120 nearer to the center front of the wearer's body (e.g., proximate to the friction buckle 112) than to the side of the wearer's body may limit the interference between the ratcheting buckle 120 and other items traditionally worn on the belt.

As shown, the raised portions of the ladder strap 102 may be arranged so as to face away from the wearer's body, avoiding the formation of pressure points at those locations. Additionally, in some embodiments, by positioning the ladder strap 102 partially between the belt 114 and the wearer's body during "normal" belt use, the ladder strap 102 may be less likely to catch on the wearer's clothes or other objects than if the ladder strap 102 were located fully on the exterior of the belt.

In the embodiments discussed above, the ladder strap 102 is arranged to pass through the slots 108 and 110 so that it is disposed between the wearer's skin and the belt material during use. In other embodiments, the ladder strap 102 may be disposed between two layers of belt material 114 created when folding the belt material 114 around the friction buckle 112, and may pass through the slot 116 to feed into the ratcheting buckle 120. In such embodiments, the slots 108 and 110 may not be present. To allow the belt material 114 to be displaced as the tourniquet is tightened (and thus not impede the tightening of the tourniquet), any stitching coupling the longitudinal edges of the two layers of belt material 114 may not be present in the vicinity of the ladder strap 102. As the tourniquet is tightened, the belt material 114 facing away from the wearer will bunch "outward," while the belt material 114 disposed between the ladder strap 102 and the wearer may bunch between the ladder strap 102 and the wearer. Since the layers of belt material 114 may not be coupled together by edge seams in the vicinity of the ladder strap 102, the bunching of the "outer" and "inner" layers may occur substantially independently.

In another embodiment, there is disclosed a tourniquet belt with an elongate belt having multiple layers of material (e.g., a flexible webbing) and an elongate tourniquet disposed in a pocket located between the layers. The tourniquet may have an end that extends through a slot or other opening at the front of the belt (e.g., near the center front of the wearer's body) such that, when the wearer grasps this exposed end and pulls, the whole tourniquet may be separated from the pocket. In some embodiments, the exposed end may have a ratcheting buckle disposed on it, for use with a ladder strap also included in the tourniquet for tightening the tourniquet.

Once separated, the tourniquet may be used to stop or slow bleeding of an injured limb. Thus, in such embodiments, the tourniquet may be stored ready to use between the layers, and may be separated from the belt when needed. Examples of suitable belts may include a two layered fabric belt or a two ply leather belt (e.g., of the type commonly worn by police officers). Any suitable dimensions may be used; for example, the belt material may have a width of 2 inches, and the tourniquet may have a width of 1.5 inches.

In some embodiments, the belt may have a slot or other opening proximate to the free end, and may be packaged with a long rod with a hook at one end for feeding the tourniquet through the pocket between the layers (in a manner similar to that used for feeding an elastic band through a waist seam). The belt may be provided with the tourniquet already disposed inside, or separately from the tourniquet. After the tourniquet is used, that tourniquet may be replaced in the belt by a new tourniquet.

Allowing a wearer to remove the tourniquet from her belt without having to remove her belt may be advantageous for wearers whose belts are used to support other equipment (such as any of the items discussed above). Because a law enforcement officer, for example, may carry so many items on her belt, it may not be possible or practical for her to remove her belt to create a tourniquet for herself or another in the face of an injury. Thus, a belt with a tourniquet that can be separated from the belt, without requiring removal of the belt, may be advantageous for such wearers.

Figure 11:
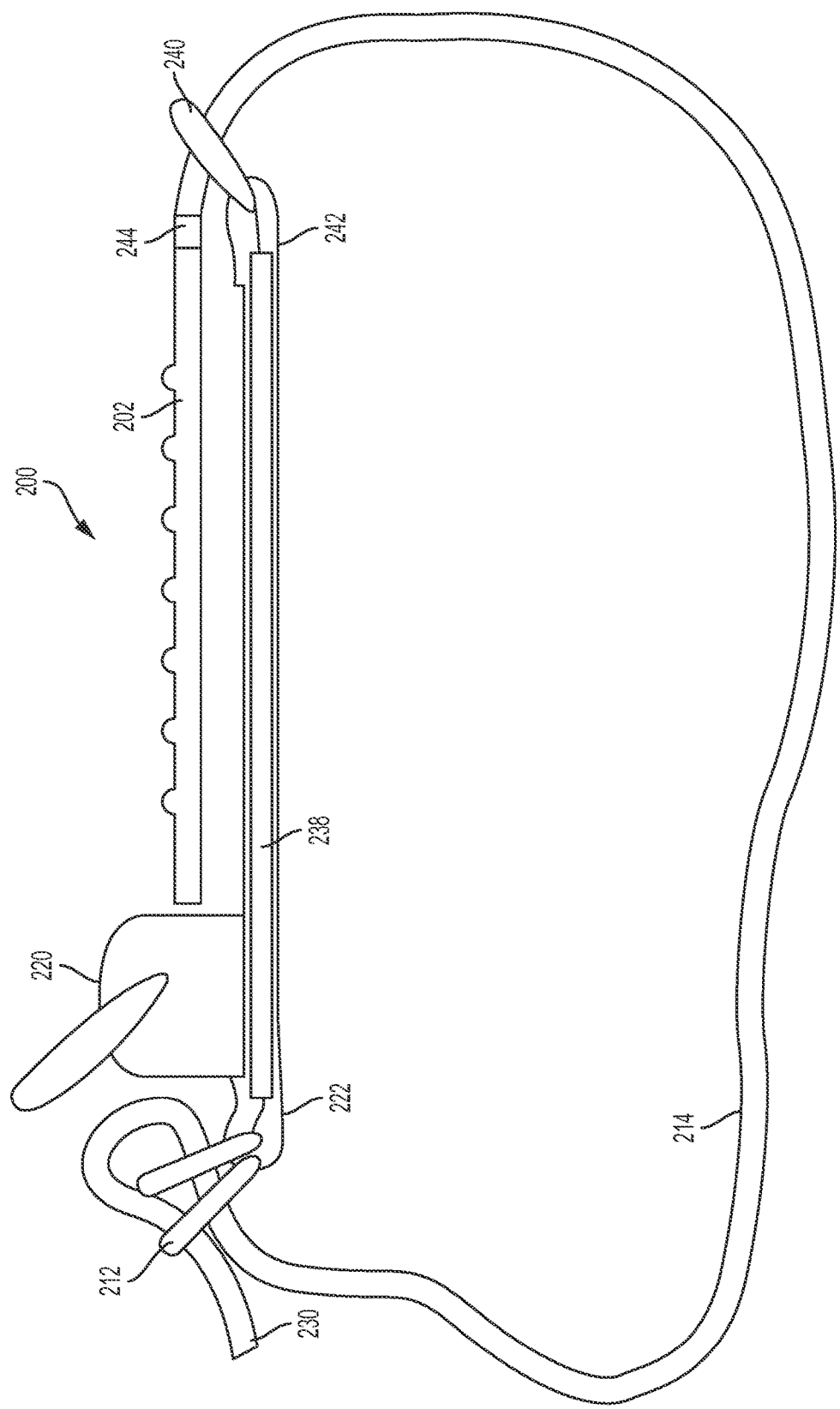
FIGS. 11-13 illustrate an alternative embodiment of a tourniquet belt in accordance with various embodiments.
Figure 12:
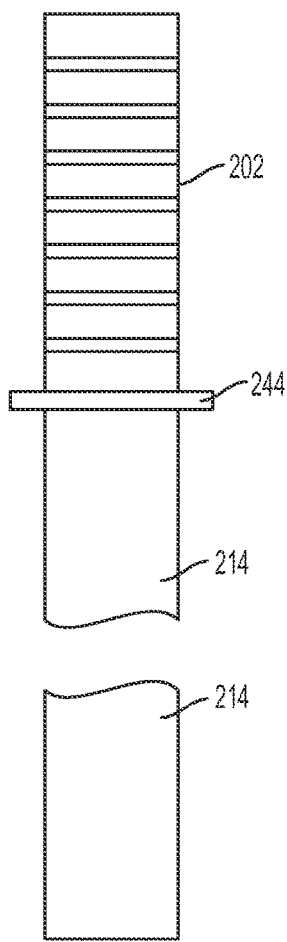
Figure 13:
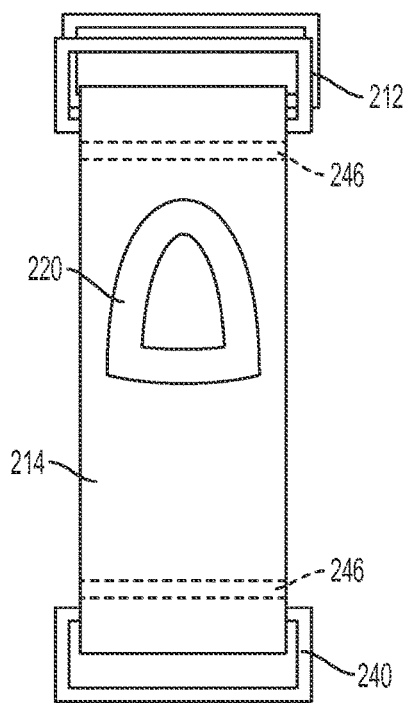

Another embodiment disclosed herein is directed to a tourniquet belt 20 that includes a ratcheting buckle 220 disposed on a support strip 238 and a ladder strap 202 that is not fixed to the support strip 238. FIGS. 11-13 illustrate various views of such an embodiment. The tourniquet belt 100 may have a friction buckle end 222 and a free end 230. The friction buckle end 222 may include a friction buckle 212 secured to a support strip 238. The free end 230 may be wound through the friction buckle 212 at the friction buckle end 222, as shown in FIG. 11. The friction buckle 212 may be a friction bar buckle, a pair of D rings, a female/male snap buckle combination, or any other suitable friction buckle (such as those discussed above).

The free end 230 may be one end of a flexible strap formed of a suitable material, such as flexible webbing or any of the belt materials discussed herein. The other end of the flexible strap may be secured to a ladder strap 202. The ladder strap 202 may be fed through a guide 240 (such as a metal ring or belt loop) disposed at the end 242 of the support strip 238 opposite to the friction buckle end 222. The ladder strap 202 may include a mechanical stop 244, which may be dimensioned so as to be too large to pass through the guide 240 and thus may prevent the ladder strap 202 from passing through the guide 240 (e.g., from left to right in the illustration of FIG. 11). The ladder strap 202 may be coupled with the ratcheting buckle 220, or may be separated from the ratcheting buckle 220 but capable of being inserted into the ratcheting buckle 220 for ratcheting during use.

The support strip 238 may be formed as a pocket of webbing or other flexible material in which a stiffener is disposed. The stiffener may be a sheet of plastic or metal, and may be dimensioned substantially as large as the pocket so as to prevent the pocket from bunching as the tourniquet belt 200 is tightened. Seams at either end of the support strip 238 may secure the friction buckle and the guide, respectively. In some embodiments, the seams 246 at either end of the support strip 238 may include a folded over portion of webbing which is secured to itself to form a channel in which the friction buckle 212 and guide 240 may be retained. This folded over portion may be arranged such that the flexible material folds toward the side of the flexible material on which the ratcheting buckle 220 is disposed and is secured on that side. Folding the flexible material in this manner may avoid having the folded over material located between the support strip 238 and the wearer's body when the tourniquet belt 200 is in use, reducing the likelihood that uncomfortable pressure points or abrasions will occur.

In use, the tourniquet belt 200 may be arranged around a wearer's limb, and initially tightened by pulling on the free end 230 in the direction of the arrow in FIG. 11. Once initially tightened, the ratcheting buckle 220 and ladder strap 202 may be ratcheted so as to move the ladder strap 202 through the ratcheting buckle 220 (from right to left in the illustration of FIG. 11), in the manner discussed above with reference to FIGS. 1-10. Since the ladder strap 202 is not fixed to the same support strip as the ratcheting buckle 220, the support strip 238 will not experience a buckling force as the ladder strap 202 moves through the ratcheting buckle 220; instead, the ladder strap 202 will move through the guide 240 to tighten without bunching. In contrast to conventional tourniquets, in which material bunches between the tourniquet and the wearer's skin during use, the tourniquet belt 200 of FIGS. 11-13 avoids bunching, improving the tourniquet performance and limiting collateral injury to the wearer.

Figure 14:
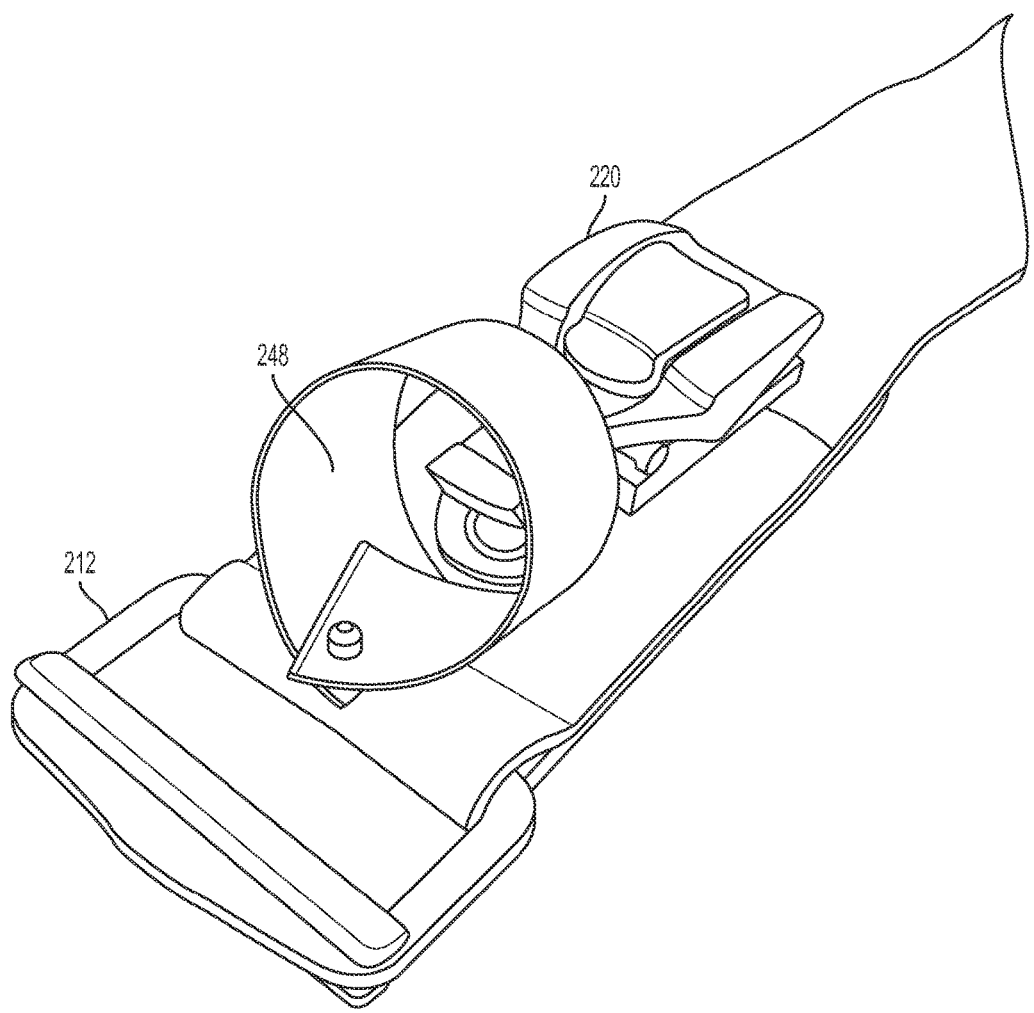
FIGS. 14 and 15 illustrate a tourniquet belt with a grasping loop in accordance with various embodiments.
Figure 15:
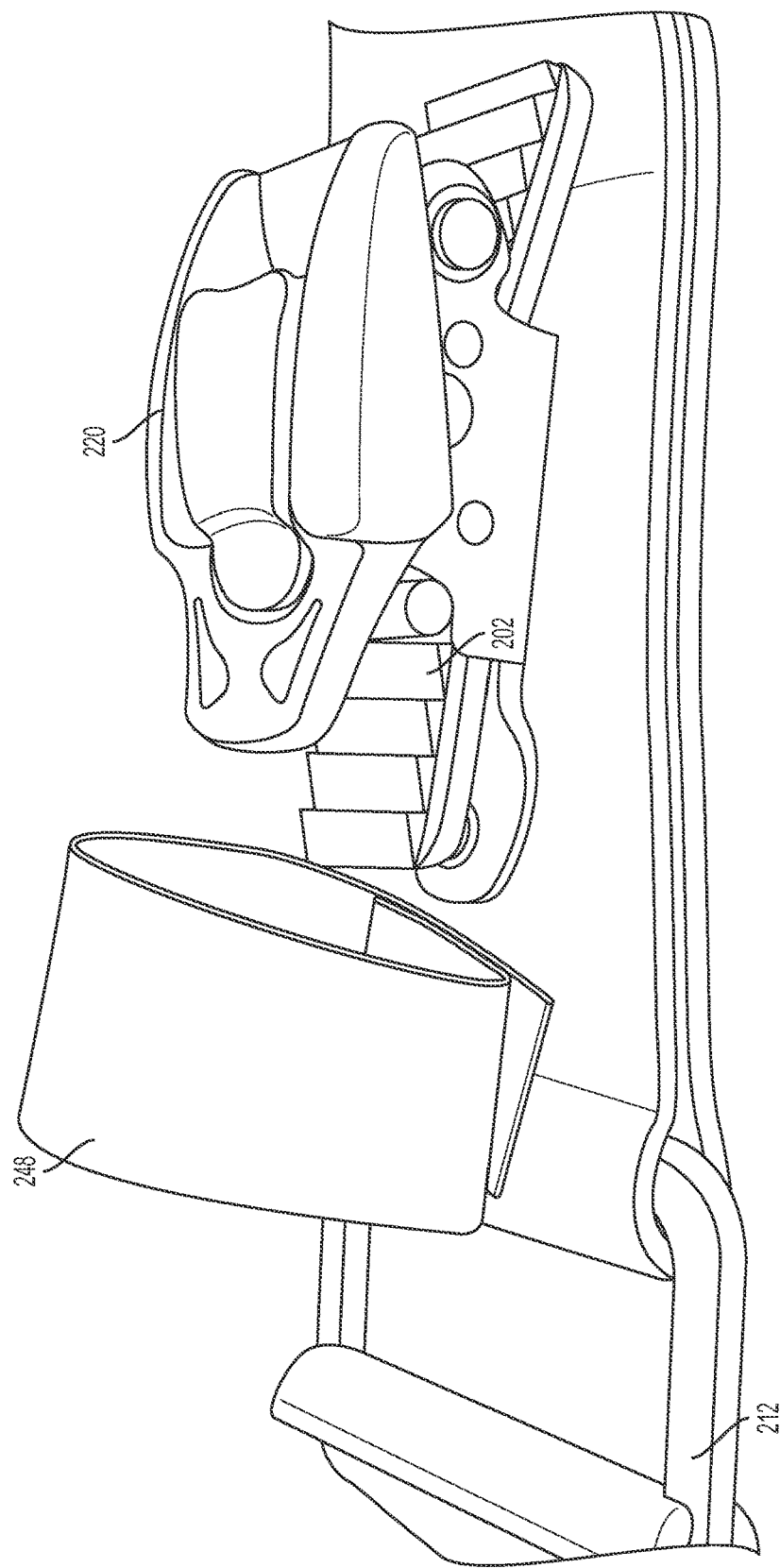

In an embodiment, the tourniquet belt 200 may also include a loop of material 248 that can be grasped to increase the wearer's grip on the tourniquet belt 200 and/or to keep the tourniquet from rotating while pulling on the free end. Examples of such an embodiment are shown in FIGS. 14 and 15. The wearer's thumb or other finger may be inserted through this loop, or the wearer may use his or her teeth to grasp the loop (e.g., if the wearer is applying the tourniquet belt to her own arm).

Figure 16:
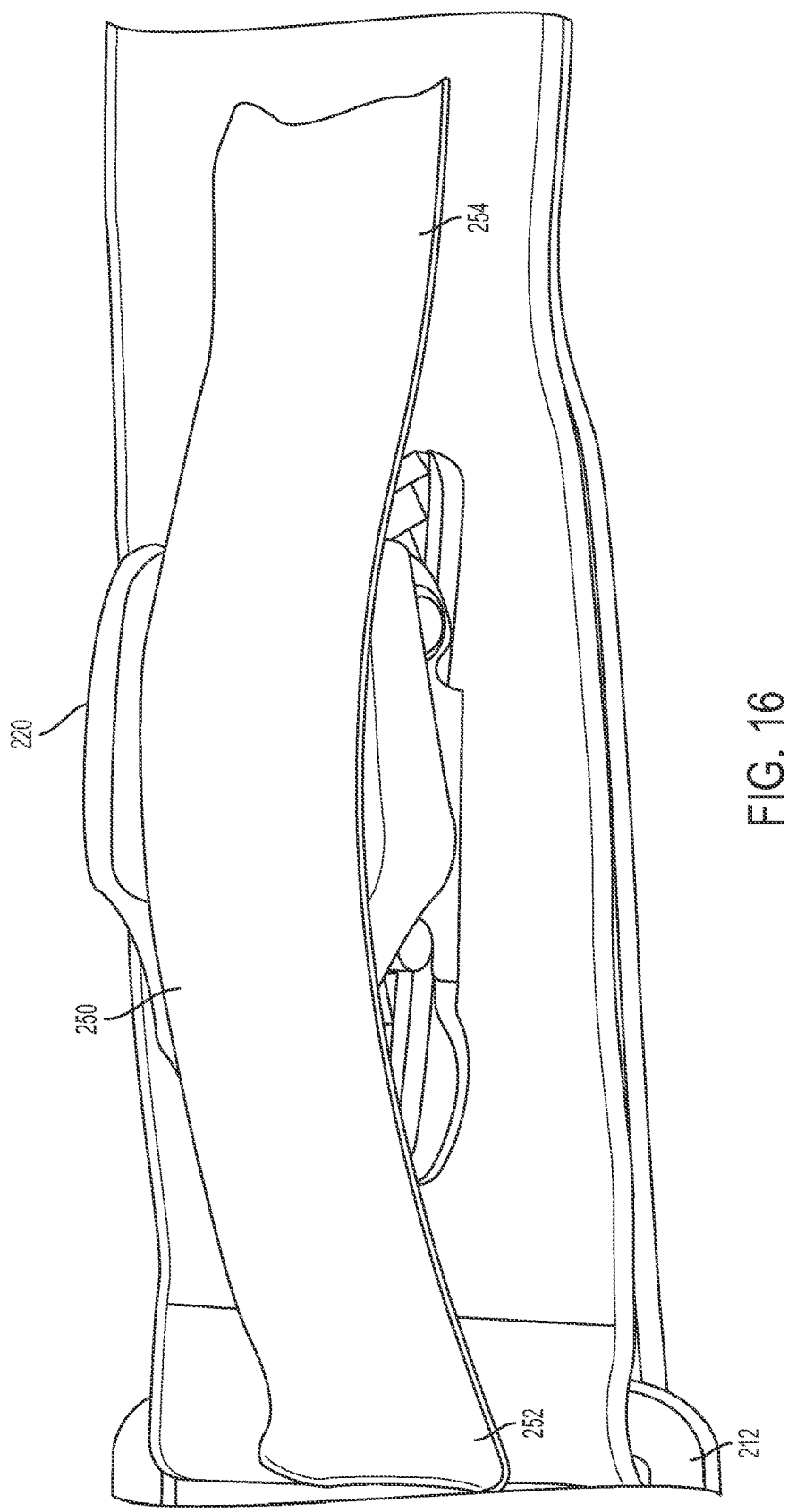
FIGS. 16 and 17 illustrate a tourniquet belt with a protective cover material over a ratcheting buckle in accordance with various embodiments.

In some embodiments of the tourniquet belt disclosed herein, a cover material 250 (e.g., nylon, se FIGS. 16 and 17) may be attached to the belt on each side of the ratchet buckle 220. An example of this arrangement is illustrated in FIG. 16. The end 252 of the cover material 250 closest to the friction buckle 212 may be permanently attached (e.g., secured in the seam) while the other end 254 of the cover material 250 farther from the friction buckle 212 may be removably attached (e.g., via a hook/loop mechanism or a snap button). This cover material 250 may act as a protective cover for the ratcheting buckle 220 so that it is not inadvertently caught on clothing or an object or ratcheted/actuated unintentionally. In use, the cover material 250 may be detached at the removable attachment point 254 to expose the ratcheting buckle 220 and allow the cover material 250 (still secured to the belt close to the friction buckle 212) to be used as a bite strap or handle during tightening of the tourniquet belt.

In some embodiments, the tourniquet belt 200 of FIGS. 11-13 may also be worn as a belt when not in use as a tourniquet. As discussed above with reference to the embodiments of FIGS. 1-10, the ratcheting buckle 220 of the tourniquet apparatus of FIGS. 11-13 is close to the friction buckle 212 (the buckle of the belt during normal use), and thus the tourniquet belt 200 of FIGS. 11-13 may have the advantages of such a configuration discussed above. Any other of the features of the embodiments discussed above with reference to FIGS. 1-10 may be applied to the embodiment of FIGS. 11-13 (e.g., the use of hook/loop or other fastening material on the free end).

Various embodiments of the tourniquet belt disclosed herein may be used in other contexts. For example, a tourniquet belt apparatus may be used as a waist strap on backpacks as a removable waist band that can also be applied as a tourniquet using the same closure design used on the belt. In some embodiments, a tourniquet belt may be used as a shoulder strap on a purse, duffel bag, or piece of equipment. In some embodiments, a tourniquet belt may be used as a rifle sling (e.g., to provide emergency tourniquet access/capability to hunters and soldiers).

As noted above, in some embodiments, the free end of a tourniquet belt may include a loop of material to assist in tightening the belt when used as a tourniquet using a thumb or the teeth, thus reducing circumferential slipping during the tightening process. In some embodiments, the friction buckle end of a tourniquet belt may include a tightening loop (e.g., instead of or in addition to a loop at the free end of the tourniquet belt). A tightening loop located at the friction buckle end may assist in tightening the belt and preventing slipping during tightening. A user's thumb can be inserted into the loop to aid in tightening by limiting or preventing the tourniquet belt from sliding around the limb during tightening. In some embodiments, the tightening loop may be grasped by a user's teeth to aid in the tightening (e.g., one being self-applied to the user's own arm). In some embodiments, a tightening loop may be formed from a webbing material.

In some embodiments, a tightening loop located at the friction buckle end and/or the free end of a tourniquet belt may be constructed so as to be maintained in a folded configuration when not in use. The folded configuration may keep the tightening loop fairly "flat" along the belt, and thus may reduce or limit the likelihood that the tightening loop will inadvertently catch on the wearer's clothes or other objects, or otherwise interfere with the wearer's activities. The folded configuration may also be readily disengaged so that the tightening loop may "expand" into an open configuration in which the user's thumb (or another object) can be inserted into the tightening loop to aid in tightening, as discussed above.

Figure 19:
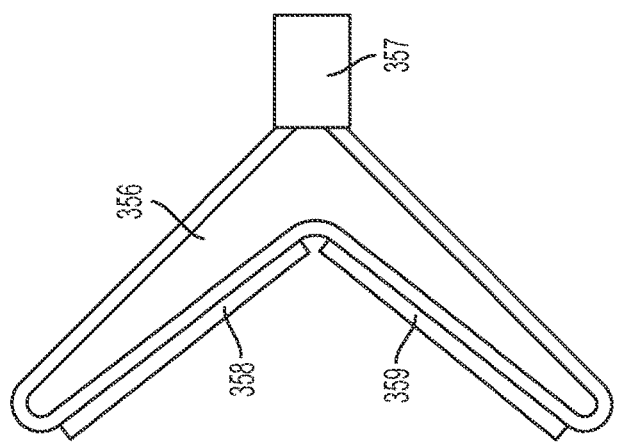
FIGS. 18-20 illustrate a tightening loop that may be engaged in a folded configuration (FIG. 20) and in an open configuration (FIG. 18) in accordance with various embodiments.
Figure 20:
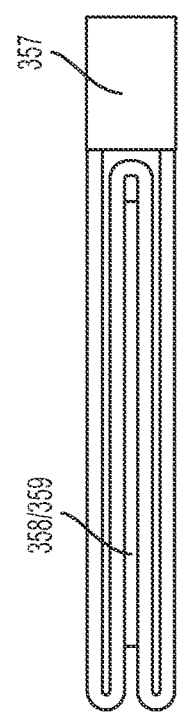
Figure 18:
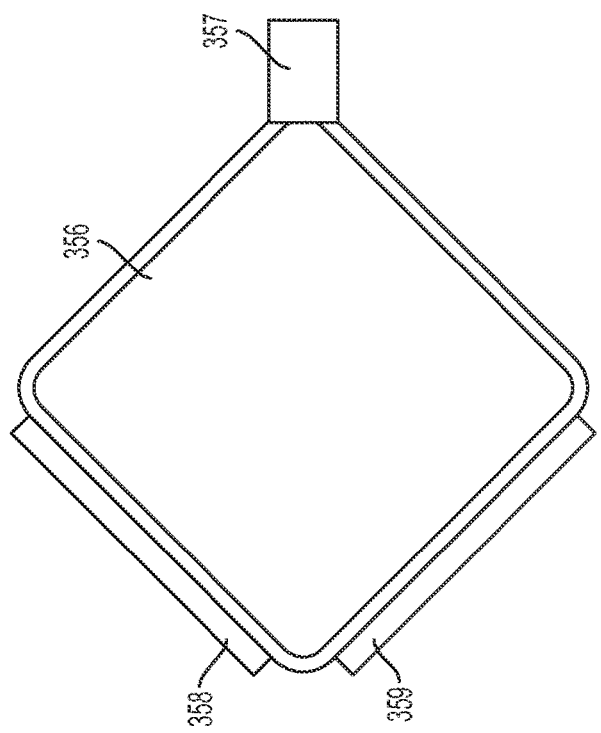

FIGS. 18-20 illustrate an embodiment of a tightening loop 356 that may be engaged in a folded configuration (FIG. 20) and in an open configuration (FIG. 18). In particular, FIG. 18 depicts a tightening loop 356 in an open configuration in which a user's thumb (or other object) may be inserted into a loop formed by a webbing material and secured at one end by a tightening loop retainer 357. The tightening loop retainer 357 may be any mechanism by which two ends of a piece of webbing or other material may be secured together to form a loop. For example, the tightening loop retainer 357 may be stitching that secures the webbing to itself and to another portion of the tourniquet belt. In some embodiments, the tightening loop retainer 357 may be a grommet or other metal fitting that secures the webbing to the belt. In some embodiments, the tightening loop retainer 357 may be stitching or a metal fitting that secures the webbing between a friction buckle and the belt of the tourniquet belt.

The tightening loop 356 of FIG. 18 includes a first piece of hook/loop material 358 and a second piece of hook/loop material 359. The hook/loop material 358 and the hook/loop material 359 are complementary (e.g., the hook/loop material 358 is hook material and the hook/loop material 359 is loop material). The hook/loop material 358 and the hook/loop material 359 may each be stitched or otherwise secured to the webbing of the tightening loop (e.g., using an adhesive).

To transition the tightening loop 356 of FIG. 18 from the open configuration to a folded configuration, the webbing of the tightening loop 356 may be folded as shown in FIG. 19 so as to position the hook/loop material 358 facing the hook/loop material 359. When the webbing of the tightening loop 256 is fully folded into the folded configuration shown in FIG. 20, the hook/loop material 358 and the hook/loop material 359 will contact each other and hold the webbing of the tightening loop 356 in the folded configuration. To transition the tightening loop 356 from the folded configuration of FIG. 20 into the open configuration of FIG. 18, a user may simply insert her finger or another object between the hook/loop material 358 and the hook/loop material 359, or in the end space between the layers of webbing proximate to the tightening loop retainer 357, and "pop" or urge the loop 356 open.

In some embodiments, the face of the webbing may be secured to the belt material of the tourniquet apparatus so that the face is permanently attached along the belt (e.g., by stitching). Such embodiments may make it easier for a user to open the tightening loop from the folded configuration because the ability of the tightening loop to move around during opening will be limited. In particular, a user may simply slide her thumb between the layers of webbing in the folded configuration from the side of the folded tightening loop to open the tightening loop and pull on it to aid in tightening.

Figure 21:
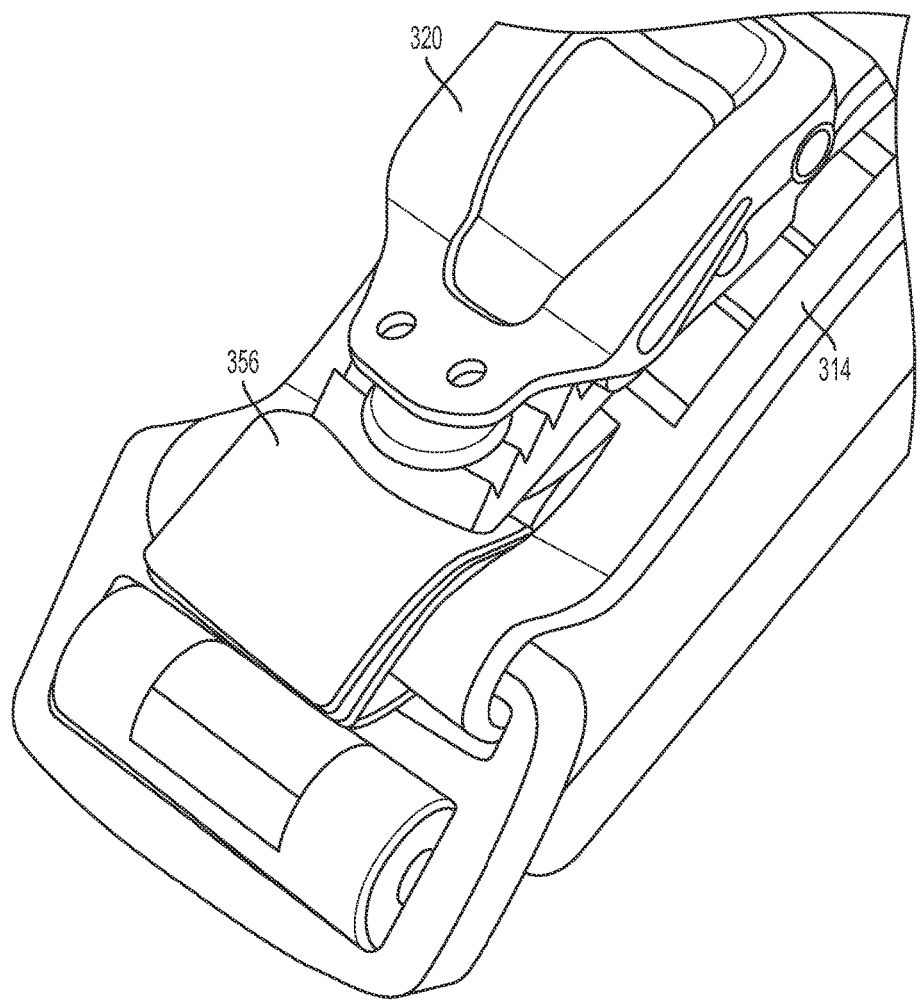
FIGS. 21 and 22 illustrate a tightening loop in accordance with various embodiments.
Figure 22:
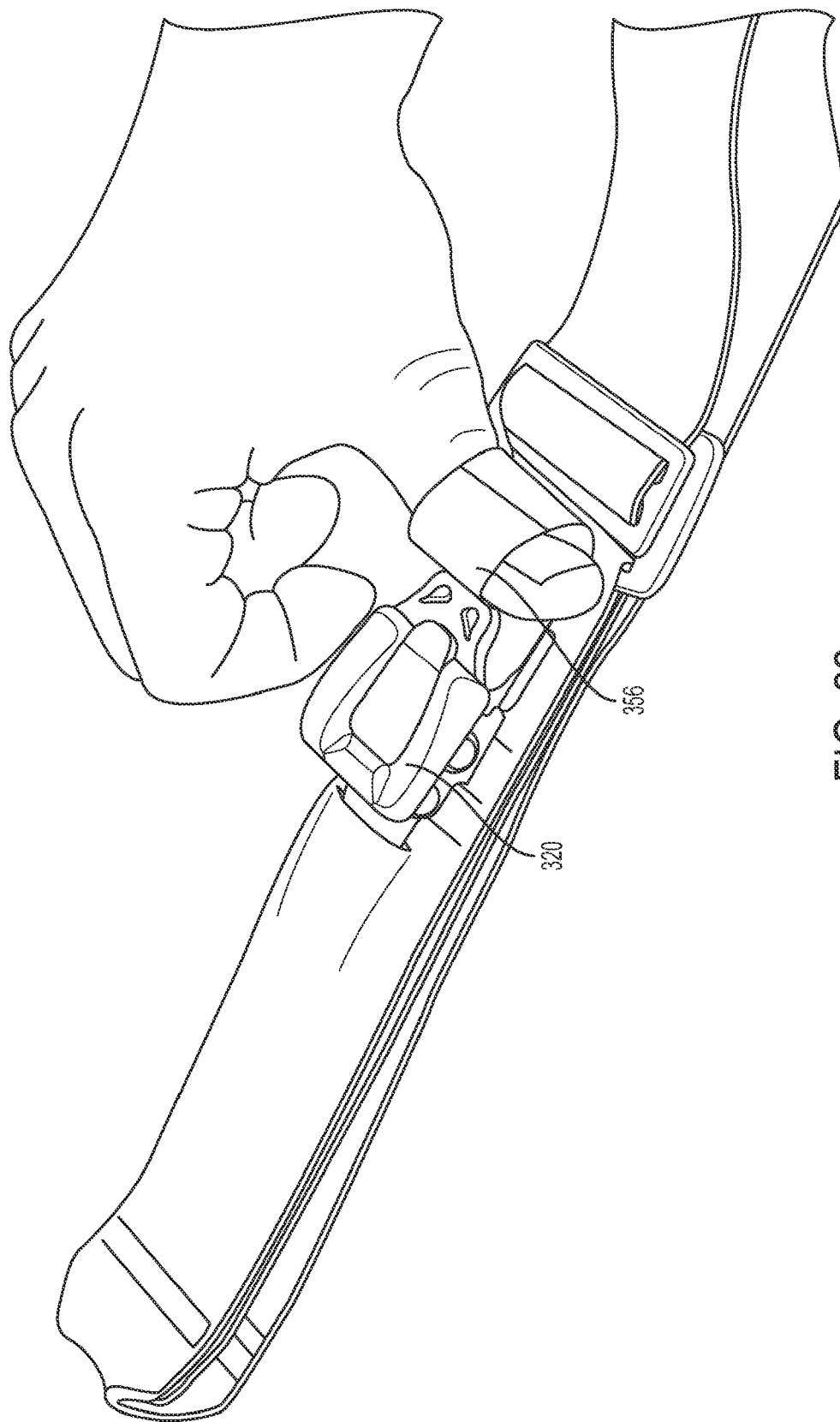

FIG. 21 depicts an embodiment of a tourniquet belt having a tightening loop 356, in a folded configuration, sandwiched between the ratcheting buckle 320 and the belt material 314 (acting as the tightening loop retainer). FIG. 22 depicts the embodiment of FIG. 21 in an open configuration with the user's thumb inserted into the tightening loop 356.

As noted above, the tourniquet belt disclosed herein may be advantageously worn as a belt for law enforcement officers, soldiers, emergency responders, or other professionals. For such wearers, belts are used to carry holsters, pagers, pepper spray, tools, medical supplies, and other job-essential items. In some embodiments, the tourniquet belt disclosed herein may include one or more accessory loops that facilitate the attachment of an accessory (such as any of those described above) to the tourniquet apparatus during use.

Figure 23:
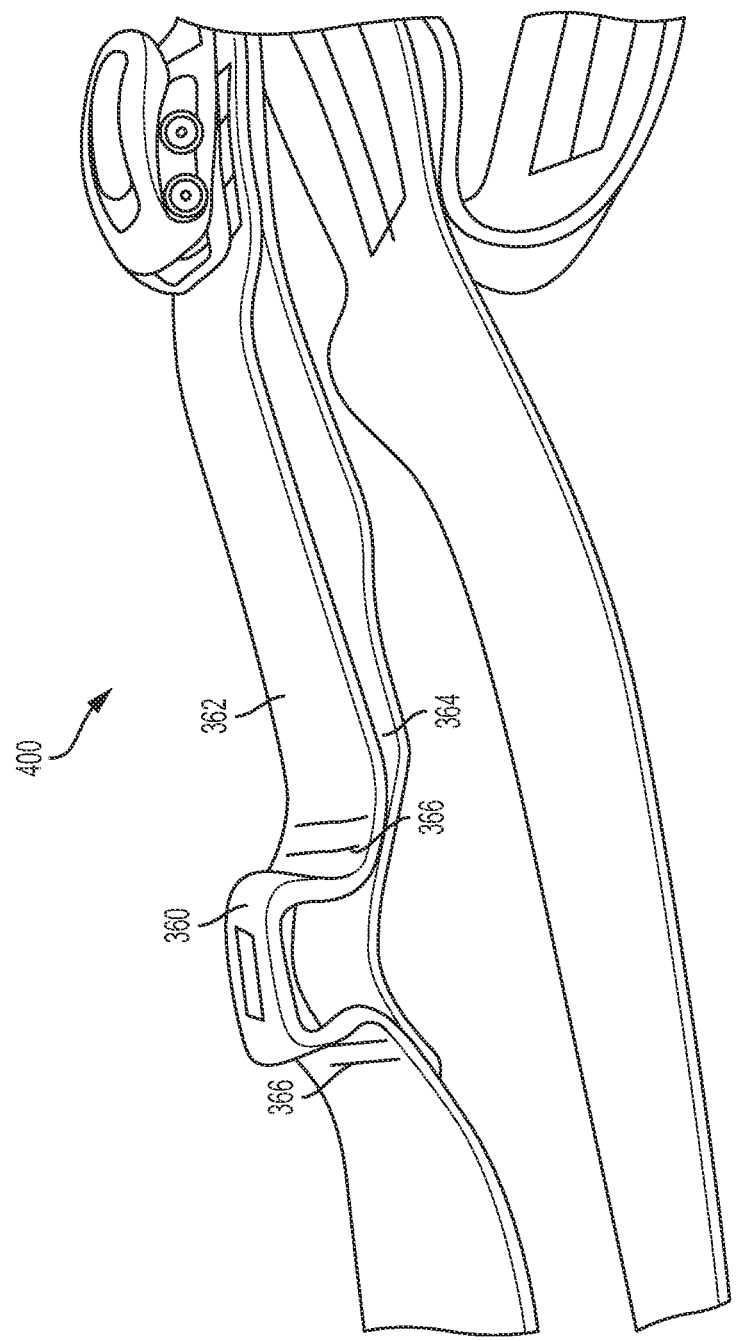
FIGS. 23 and 24 illustrate an accessory loop in accordance with various embodiments.
Figure 24:
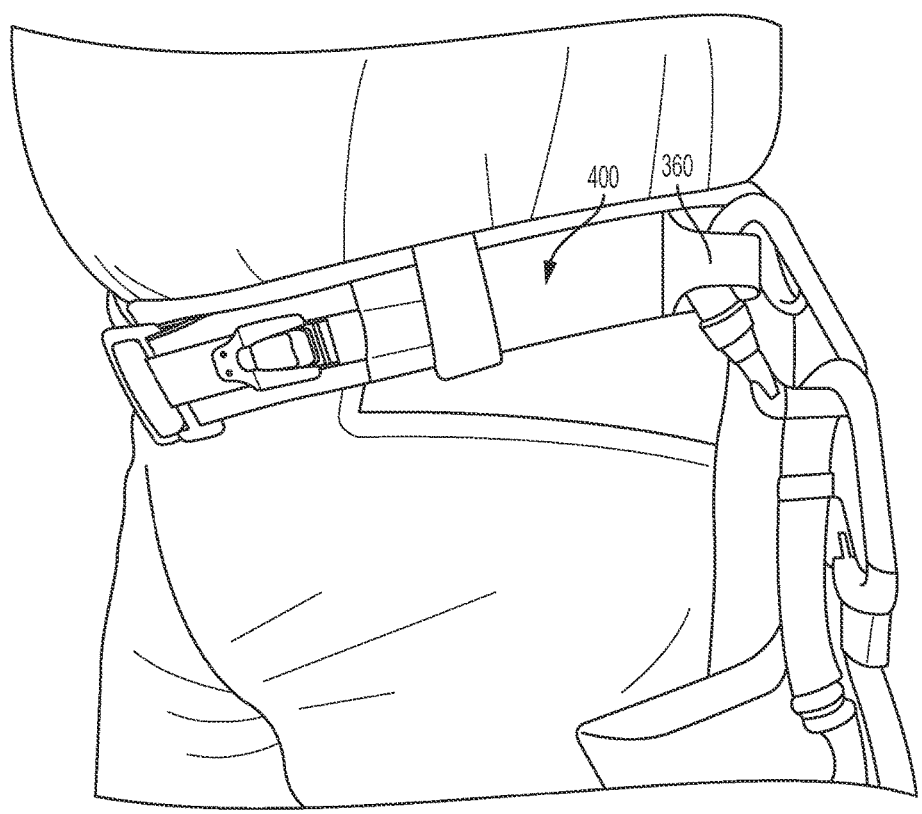

In some embodiments, an accessory loop 360 may be formed using a two layer construction, as illustrated in FIG. 23. A first layer of material 362 may be secured at two attachment locations to a second layer of material 364. "Slack" in the first layer of material 362 between the two attachment locations may provide an area between the layers of material 362,364, thus forming the accessory loop 360, as shown. In some embodiments, the "slack" in the first layer of material 362 may be folded over and secured to itself by stitching 366, as shown, to increase the rigidity of the accessory loop 360 and reduce the likelihood that it will collapse. In some embodiments, bar tacks may be stitched into the tourniquet belt 400 proximate to the attachment locations to improve the resistance of the tourniquet belt 400 to the forces caused when an accessory "weighs down" the accessory loop 360 during use. FIG. 24 depicts the tourniquet belt 400 of FIG. 23 in use, and in particular, depicts a carabiner supported by the accessory loop 360. The accessory loop 360 may be dimensioned in any desired and suitable manner (e.g., to accommodate various accessories), and some embodiments of the tourniquet belt 400 disclosed herein may include multiple accessory loops (which may have different sizes).

In some embodiments, a tourniquet belt may serve as a harness (or part of a harness) for securing a wearer to another structure, and an accessory loop may serve as an attachment point for cables or other straps between the harness and the structure. For example, a soldier, riding in an airplane or helicopter and wearing one of the tourniquet apparatuses disclosed herein as a belt, may clip one end of an airplane lanyard into an accessory loop on the tourniquet apparatus while the other end is secured to the floor or a wall of the airplane (to constrain the soldier from being thrown around in the airplane or helicopter during flight). In this manner, the tourniquet belt may serve as a portable seatbelt. In some embodiments, the tourniquet belt may be rated as a harness (e.g., tested to ensure that it can support a predetermined amount of weight with a certain probability), and thus may be configured to serve as a life-saving attachment for workers performing tasks (or sports enthusiasts engaging in sports) off the ground.

As discussed above with reference to FIG. 23, stitching may be used to stiffen portions of the belt material of the tourniquet apparatus. In particular, a line of stitching in the belt may improve the resistance of the belt to bending in a direction perpendicular to the line of stitching (in the area of the line of stitching). The additional resistance imparted by the line of stitching may depend on the stiffness of the thread used to perform the stitching, the size of the stitches, and the density of multiple stitched lines, among other factors. Such stitching may be included anywhere along the belt of a tourniquet belt, and may be particularly useful in locations where the wearer of the tourniquet belt is likely to mount an item such as a handgun or heavy pouch. In those locations, the stitching may provide extra stability to the tourniquet belt so that the material (e.g., webbing) is more resistant to buckling under the weight of the attached object. Additionally, by selectively including stitching to improve bending resistance at only certain locations in the tourniquet belt, it may not be necessary to use an extremely stiff material throughout the tourniquet belt and instead, other locations of the tourniquet belt may maintain their flexibility.

FIGS. 25 and 26 illustrate various examples of stitching that may impart additional stiffness to the belt of a tourniquet belt in one or more directions. In particular, FIG. 25 illustrates stitching 568 arranged in an "X" pattern, lines of stitching 570 in the longitudinal direction of the belt material, and lines of stitching 572 in the lateral direction of the belt 514. The stitching arrangement of FIG. 25 may impart additional resistance to bending of the belt 514 in both the lateral direction and the longitudinal direction.

FIG. 26 illustrates stitching arranged as "bar tacks" extending in the lateral direction of the belt 514. Bar tacks 574 may improve the resistance of the belt 514 to "pinching" in the lateral direction, but may not substantially impede the longitudinal flexibility of the belt 514.

Although certain arrangements of stitching are shown and discussed with reference to FIGS. 25 and 26, any suitable pattern of stitching may be included to achieve a desired improvement stiffness. For example, in some embodiments, the stitching may take the form of a company logo or product name embroidered into the belt material using a heavy-duty thread. Such an embroidered logo may provide both stiffening and product identification.

In some embodiments, a tourniquet belt with a ratcheting buckle may include a protective cover for the ratcheting buckle. The protective cover may snap or otherwise fit over the ratcheting buckle, and may largely conform to the shape of the ratcheting buckle. The protective cover may also be readily removable so that a user can access the ratcheting buckle in an emergency. The protective cover may provide abrasion resistance to the ratcheting buckle and/or may repel dust and dirt. For example, the protective cover may mitigate or prevent damage to the ratcheting buckle during daily wear of the tourniquet belt (e.g., when the wearer climbs over a wall or crawls on the ground "stomach down"). In some embodiments, the protective cover may be formed from a thermoplastic, such as KYDEX (manufactured by Kydex, LLC of Nevada).

Figure 29:
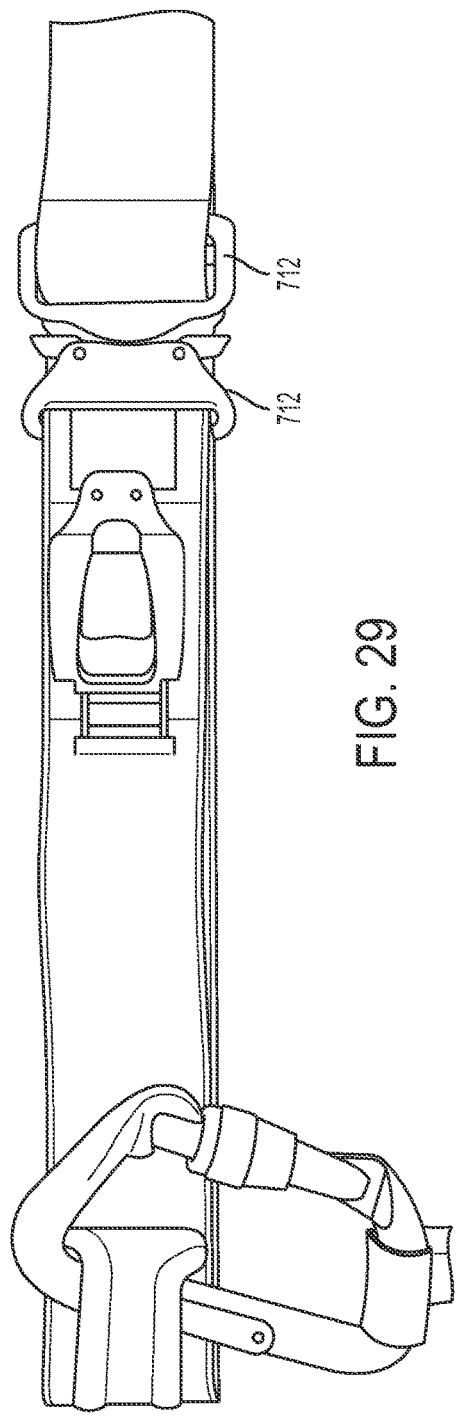
Figure 30:
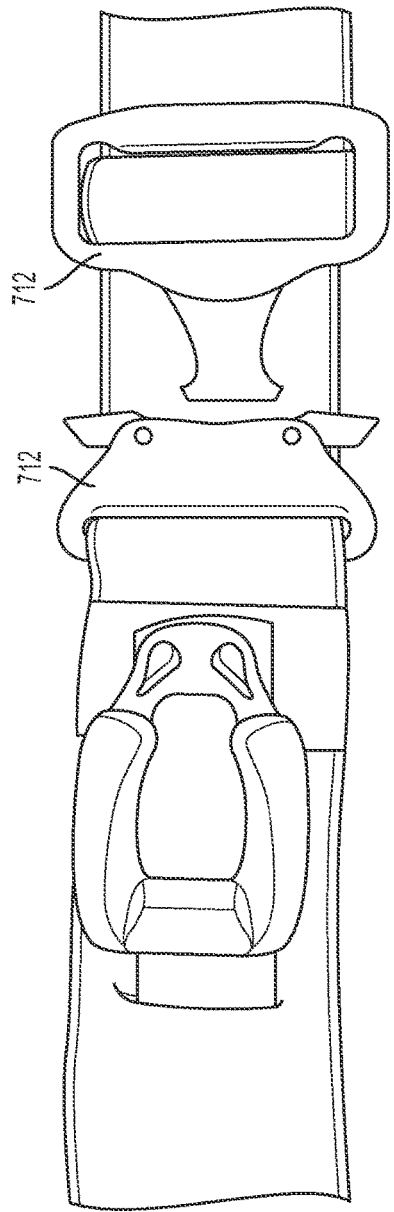

Many of the embodiments discussed herein have referred to a friction buckle that secures a free end of the tourniquet apparatus. Suitable friction buckles that may be used for this purpose may include one piece friction buckles or two piece friction buckles. For example, FIGS. 27 and 28 illustrate embodiments using a one piece friction buckle 612, while FIGS. 29 and 30 illustrate embodiments using a two-piece friction buckle 712. Different buckles may be suitable for different applications (e.g., based on user preference).

Figure 31:
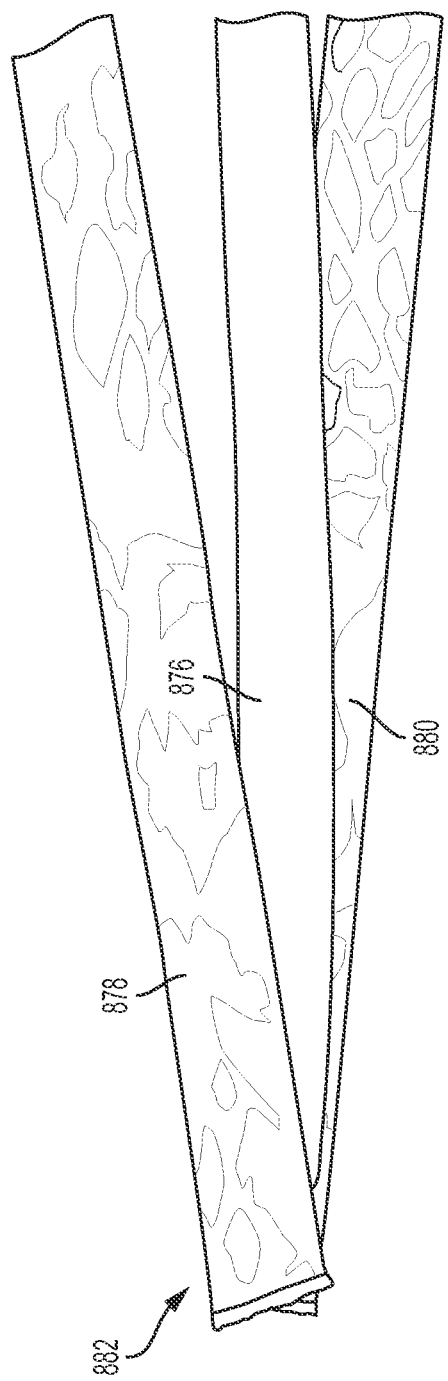
FIGS. 31-33 illustrate alternative arrangements of tourniquet belts in accordance with various embodiments.
Figure 32:
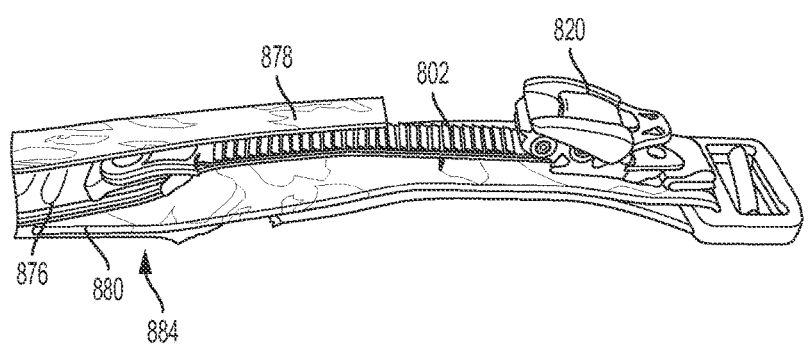
Figure 33:
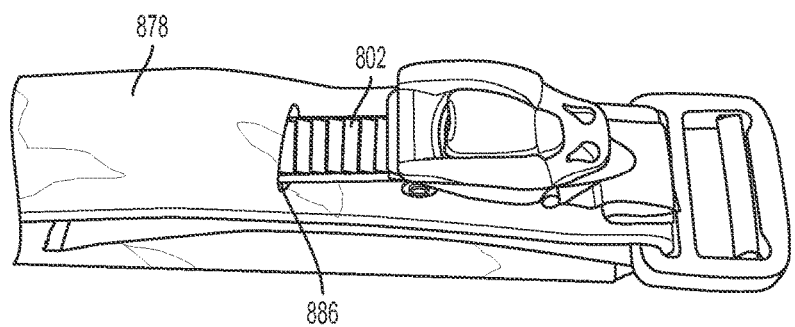

Belts in accordance with embodiments herein may be constructed in a variety of ways as discussed above, and in others known in the relevant industries. In accordance with one embodiment, a belt may be constructed with three layers of material as shown in FIGS. 31-33. In such a structure, the center layer 876 may be narrower than the top layer 878 and bottom layer 880 and may be secured to the outer layers 878, 880 at one end 882. The unsecured end 884 of the center layer 876 may be attached to a ladder strap 802. The ladder strap 802 may be unattached from the outer two layers 878, 880. When used as a tourniquet, the tightening of the ratcheting buckle 820 pulls the center strap 876 tight but eliminates or reduces bunching of the outer two layers 878, 880. The top layer 878 may be sized to end along the length of the ladder strap 802 (see FIG. 32) or an opening 886 may be formed in top layer 878 through which ladder strap 802 may pass (see FIG. 33).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A tourniquet belt, comprising:
an elongate belt having a first end and a second free end;
a ladder strap coupled to the elongate belt at a first end of the ladder strap;
a securing element coupled to the elongate belt at the first end of the elongate belt and configured to secure the second free end of the elongate belt; and
a separate tightening element coupled to the elongate belt, wherein the tightening element comprises a ratcheting buckle configured to engage the ladder strap, wherein the ratcheting buckle is selectively actuable to tighten or loosen the tourniquet belt, and wherein the ladder strap is coupled to an interior surface of the belt and the ladder strap extends through the bell to engage with the tightening element.

2. The tourniquet belt of claim 1, wherein the tightening element is permanently attached to the belt at a position closer to the first end than to the second free end of the elongate belt.

3. The tourniquet belt of claim 1, wherein the securing element is a friction buckle.

4. The tourniquet belt of claim 1, wherein the ratcheting buckle includes a handle that is selectively actuable to advance the ladder strap relative to the ratcheting buckle.

5. The tourniquet belt of claim 1, further comprising a release configured to disengage the ratcheting buckle from the ladder strap.

6. The tourniquet belt of claim 1, further comprising a protective cover covering a portion of the ladder strap.

7. The tourniquet belt of claim 1, further comprising a protective cover covering at least a portion of the tightening element.

8. The tourniquet belt of claim 1, wherein a first face of the second free end of the belt comprises a first securing feature at a first location, and the first face of the belt has a second complementary securing feature at a second location.

9. The tourniquet belt of claim 1, wherein the elongate belt comprising three layers of material coupled together.

\* \* \* \* \*